(12) United States Patent
Kim

(10) Patent No.: US 11,554,144 B2
(45) Date of Patent: Jan. 17, 2023

(54) NANOVESICLES DERIVED FROM ENHYDROBACTER BACTERIA, AND USE THEREOF

(71) Applicant: MD HEALTHCARE INC., Seoul (KR)

(72) Inventor: Yoon-Keun Kim, Paju-Si (KR)

(73) Assignee: MD HEALTHCARE INC., Seoul (KR)

( * ) Notice: Subject to any disclaimer, the term of this patent is extended or adjusted under 35 U.S.C. 154(b) by 253 days.

(21) Appl. No.: 16/978,562

(22) PCT Filed: Mar. 5, 2019

(86) PCT No.: PCT/KR2019/002503
§ 371 (c)(1),
(2) Date: Sep. 4, 2020

(87) PCT Pub. No.: WO2019/172600
PCT Pub. Date: Sep. 12, 2019

(65) Prior Publication Data
US 2021/0015875 A1 Jan. 21, 2021

(30) Foreign Application Priority Data

Mar. 5, 2018 (KR) .................. 10-2018-0026037
Mar. 4, 2019 (KR) .................. 10-2019-0024890

(51) Int. Cl.
| A61K 39/02 | (2006.01) |
| A61K 35/74 | (2015.01) |
| A61P 9/10 | (2006.01) |
| A61P 3/10 | (2006.01) |
| A61P 35/00 | (2006.01) |
| C12Q 1/6844 | (2018.01) |
| A61K 39/00 | (2006.01) |

(52) U.S. Cl.
CPC ............... *A61K 35/74* (2013.01); *A61P 3/10* (2018.01); *A61P 9/10* (2018.01); *A61P 35/00* (2018.01); *C12Q 1/6844* (2013.01); *A61K 2039/52* (2013.01)

(58) Field of Classification Search
CPC ..................................................... A61K 35/74
See application file for complete search history.

(56) References Cited

U.S. PATENT DOCUMENTS

2011/0229916 A1   9/2011  Reneker et al.
2014/0044677 A1*  2/2014  Qvit-Raz ............... A61K 8/27
                                                    435/252.32

FOREIGN PATENT DOCUMENTS

| CN | 102480932 A | 5/2012 |
| CN | 102549143 A | 7/2012 |
| CN | 103237901 A | 8/2013 |
| CN | 105407728 A | 3/2016 |
| CN | 106535907 A | 3/2017 |
| CN | 107429290 A | 12/2017 |
| CN | 107541544 A | 1/2018 |
| CN | 107750161 A | 3/2018 |
| JP | 2009-536313 A | 10/2009 |
| KR | 10-2008-0077140 A | 8/2008 |
| KR | 10-2011-0025068 A | 3/2011 |
| KR | 10-2011-0115591 A | 10/2011 |
| KR | 10-1361730 B1 | 2/2014 |
| KR | 10-2016-0073157 A | 6/2016 |
| KR | 10-2017-0127758 A | 11/2017 |
| KR | 10-2018-0006303 A | 1/2018 |
| KR | 10-2018-0018354 A | 2/2018 |
| KR | 10-1833348 B1 | 3/2018 |
| WO | 2009/018447 A2 | 2/2009 |
| WO | 2018/008895 A1 | 1/2018 |
| WO | 2018/111040 A1 | 6/2018 |
| WO | 2018/124606 A1 | 7/2018 |
| WO | 2018/155950 A1 | 8/2018 |
| WO | 2018/155960 A1 | 8/2018 |

OTHER PUBLICATIONS

Office Action dated Sep. 14, 2021 for Japanese Patent Application No. 2020-546473.
EESR dated Nov. 2, 2021 for European Patent Application No. 19763721.8.
Office Action dated Dec. 9, 2021 for the corresponding Chinese Patent Application No. 201980017161.2.

* cited by examiner

*Primary Examiner* — Albert M Navarro
(74) *Attorney, Agent, or Firm* — Vorys, Sater, Seymour and Pease LLP; Mih Suhn Koh

(57) ABSTRACT

Provided are vesicles derived from *Enhydrobacter* bacteria and a use thereof, and the inventors experimentally confirmed that the vesicles were significantly reduced in clinical samples obtained from patients with pancreatic cancer, cholangiocarcinoma, breast cancer, ovarian cancer, lymphoma, myocardial infarction, cardiomyopathy, atrial fibrillation, variant angina, liver cirrhosis, and diabetes, compared with a normal individual, and that when vesicles isolated from the strain were administered, the secretion of inflammatory mediators caused by pathogenic vesicles, such as *E. coli*-derived vesicles, was significantly inhibited. Therefore, it is expected that the vesicles derived from *Enhydrobacter* bacteria according to the present invention can be effectively used for a method of diagnosing pancreatic cancer, cholangiocarcinoma, breast cancer, ovarian cancer, lymphoma, myocardial infarction, cardiomyopathy, atrial fibrillation, variant angina, liver cirrhosis, or diabetes, and for developing a composition for preventing, alleviating or treating the diseases.

4 Claims, 9 Drawing Sheets
Specification includes a Sequence Listing.

NANOVESICLES DERIVED FROM ENHYDROBACTER BACTERIA, AND USE THEREOF

CROSS-REFERENCE TO RELATED APPLICATIONS

This application is a 371 of PCT/KR2019/002503, filed Mar. 5, 2019, which claims the benefit of priority from Korean Patent Application No. 10-2018-0026037, filed Mar. 5, 2018 and Korean Patent Application No. 10-2019-0024890 filed Mar. 4, 2019, the contents of each of which are incorporated herein by reference in its entirety.

SEQUENCE LISTING

The Sequence Listing submitted in text format (.txt) filed on Sep. 4, 2020, named "SequenceListing.txt", created on Aug. 31, 2020 (732 bytes), is incorporated herein by reference.

TECHNICAL FIELD

The present invention relates to nanovesicles derived from *Enhydrobacter* bacteria and a use thereof, and more particularly, to a method of diagnosing pancreatic cancer, cholangiocarcinoma, breast cancer, ovarian cancer, lymphoma, myocardial infarction, cardiomyopathy, atrial fibrillation, variant angina, liver cirrhosis, or diabetes using nanovesicles derived from *Enhydrobacter* bacteria, and a composition for preventing, alleviating or treating the disease, which comprises the vesicles.

BACKGROUND ART

Since the beginning of the 21st century, acute infectious diseases recognized as epidemic diseases in the past have become less important, whereas chronic inflammatory diseases accompanied by immune dysfunction caused by disharmony between humans and microbiomes have changed disease patterns as main diseases that determine the quality of life and the human lifespan. As an intractable chronic disease in the 21st century, cancer, cardiovascular diseases, chronic lung diseases, metabolic diseases, and neuropsychiatric diseases have become a big problem for public health in the country as main diseases that determine the human lifespan and the quality of life.

It is known that the number of microorganisms coexisting in the human body has reached 100 trillion, which is 10 times more than the number of human cells, and the number of microorganism genes is more than 100 times the number of human genes. A microbiota or microbiome refers to a microbial community including bacteria, archaea and eukarya present in a given habitat.

Bacteria coexisting in our body and bacteria present in the ambient environment secrete nanometer-sized vesicles in order to exchange information on genes, low molecular compounds, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa. Bacteria-derived vesicles that are locally secreted from bacteria are absorbed via epithelial cells of the mucous membrane to thereby induce a local inflammatory response, and the vesicles having passed through the epithelial cells are systematically absorbed via lymphatic vessels and thereby distributed in respective organs, and immune and inflammatory responses are regulated in the organs in which the vesicles are distributed. For example, vesicles derived from pathogenic gram-negative bacteria such as *Escherichia coli* locally cause inflammatory response and cancer, and promote a systemic inflammatory response, and blood coagulation through a vascular endothelial inflammatory response when absorbed into blood vessels, and cause insulin resistance and diabetes when absorbed into insulin-acting muscle cells. On the other hand, vesicles derived from beneficial bacteria may control a disease by controlling immune dysfunction and metabolic dysfunction caused by pathogenic vesicles.

As immune responses to factors such as bacteria-derived vesicles, Th17 immune responses characterized by the secretion of the interleukin (hereinafter, IL)-17 cytokine occur, and IL-6 is secreted when exposed to bacteria-derived vesicles, thereby inducing Th17 immune responses. Inflammation caused by the Th17 immune response is characterized by neutrophil infiltration, and during the process by which inflammation occurs, tumor necrosis factor-alpha (hereinafter, TNF-α) secreted from inflammatory cells such as macrophages plays an important role.

*Enhydrobacter* bacteria are gram-negative bacteria belonging to the class Alphaproteobacteria. *Enhydrobacter aerosaccus* is the only species belonging to the genus *Enhydrobacter*, known as a catalase- and oxidase-positive bacterium. However, the fact that vesicles are not secreted from *Enhydrobacter* bacteria to the outside of the cells has not been reported yet, and no case in which *Enhydrobacter*-derived vesicles are applied to diagnosis and treatment of intractable diseases such as cancer, a cardiovascular disease and diabetes has been reported.

DISCLOSURE

Technical Problem

As a result of earnest research to solve the conventional problems, the inventors confirmed that the content of vesicles derived from *Enhydrobacter* bacteria significantly decreased in samples obtained from patients with pancreatic cancer, cholangiocarcinoma, breast cancer, ovarian cancer, lymphoma, myocardial infarction, cardiomyopathy, atrial fibrillation, variant angina, liver cirrhosis, and diabetes, compared with a normal person, through metagenomic analysis. In addition, it was confirmed that when macrophages were treated with vesicles isolated from *Enhydrobacter aerosaccus* belonging to *Enhydrobacter* bacteria, IL-6 and TNF-α secretion mediated by pathogenic vesicles was significantly inhibited, and based on this, the present invention was completed.

Thus, an object of the present invention is to provide a method of providing information for diagnosis of pancreatic cancer, cholangiocarcinoma, breast cancer, ovarian cancer, lymphoma, myocardial infarction, cardiomyopathy, atrial fibrillation, variant angina, liver cirrhosis, or diabetes.

Further, another object of the present invention is to provide a composition for preventing, alleviating or treating pancreatic cancer, cholangiocarcinoma, breast cancer, ovarian cancer, lymphoma, myocardial infarction, cardiomyopathy, atrial fibrillation, variant angina, liver cirrhosis, or diabetes, comprising vesicles derived from *Enhydrobacter* bacteria as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a method of providing information for diagnosing pancreatic cancer, cholangiocarcinoma, breast cancer, ovarian cancer, lymphoma, myocardial infarction, cardiomyopathy, atrial fibrillation, variant angina, liver cirrhosis, or diabetes, the method comprising the following steps:

(a) extracting DNAs from extracellular vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) classifying a case in which a content of extracellular vesicles derived from *Enhydrobacter* bacteria is lower than that of the normal individual sample, as pancreatic cancer, cholangiocarcinoma, breast cancer, ovarian cancer, lymphoma, myocardial infarction, cardiomyopathy, atrial fibrillation, variant angina, liver cirrhosis, or diabetes, through quantitative analysis of the PCR product.

In addition, the present invention provides a method of diagnosing pancreatic cancer, cholangiocarcinoma, breast cancer, ovarian cancer, lymphoma, myocardial infarction, cardiomyopathy, atrial fibrillation, variant angina, liver cirrhosis, or diabetes, the method comprising the following steps:

(a) extracting DNAs from extracellular vesicles isolated from samples of a normal individual and a subject;

(b) performing polymerase chain reaction (PCR) on the extracted DNA using a pair of primers prepared based on a gene sequence present in 16S rDNA to obtain each PCR product;
and (c) determining a case in which a content of extracellular vesicles derived from *Enhydrobacter* bacteria is lower than that of the normal individual sample, as pancreatic cancer, cholangiocarcinoma, breast cancer, ovarian cancer, lymphoma, myocardial infarction, cardiomyopathy, atrial fibrillation, variant angina, liver cirrhosis, or diabetes, through quantitative analysis of the PCR product.

As an embodiment of the present invention, the sample in Step (a) may be blood.

As another embodiment of the present invention, the primer pair in Step (b) may be primers of SEQ ID Nos. 1 and 2.

Further, the present invention provides a pharmaceutical composition for preventing or treating pancreatic cancer, cholangiocarcinoma, breast cancer, ovarian cancer, lymphoma, myocardial infarction, cardiomyopathy, atrial fibrillation, variant angina, chronic liver diseases, or diabetes, comprising vesicles derived from *Enhydrobacter* bacteria as an active ingredient.

Further, the present invention provides a food composition for preventing or alleviating pancreatic cancer, cholangiocarcinoma, breast cancer, ovarian cancer, lymphoma, myocardial infarction, cardiomyopathy, atrial fibrillation, variant angina, chronic liver diseases, or diabetes, comprising vesicles derived from *Enhydrobacter* bacteria as an active ingredient.

Further, the present invention provides a use of vesicles derived from *Enhydrobacter* bacteria for preventing or treating pancreatic cancer, cholangiocarcinoma, breast cancer, ovarian cancer, lymphoma, myocardial infarction, cardiomyopathy, atrial fibrillation, variant angina, chronic liver diseases, or diabetes.

Further, the present invention provides a method of preventing or treating pancreatic cancer, cholangiocarcinoma, breast cancer, ovarian cancer, lymphoma, myocardial infarction, cardiomyopathy, atrial fibrillation, variant angina, chronic liver diseases, or diabetes, the method comprising a step of administering a pharmaceutical composition comprising vesicles derived from *Enhydrobacter* bacteria as an active ingredient to a subject.

In one embodiment of the present invention, the vesicles may have an average diameter of 10 to 200 nm.

In another embodiment of the present invention, the vesicles may be secreted naturally or artificially from *Enhydrobacter* bacteria.

In another embodiment of the present invention, the vesicles derived from *Enhydrobacter* bacteria may be vesicles derived from *Enhydrobacter aerosaccus*.

Advantageous Effects

The inventors confirmed that intestinal bacteria are not absorbed into the body through epithelial cells, but bacteria-derived vesicles are absorbed, systemically distributed and then excreted out of the body through the kidneys, liver and lungs, and by metagenomic analysis for vesicles derived from bacteria present in patients' blood, also confirmed that vesicles derived from *Enhydrobacter* bacteria, which are present in blood of patients with pancreatic cancer, cholangiocarcinoma, breast cancer, ovarian cancer, lymphoma, myocardial infarction, cardiomyopathy, atrial fibrillation, variant angina, liver cirrhosis, and diabetes significantly decrease, compared with a normal individual. In addition, when *Enhydrobacter aerosaccus*, which is one species of *Enhydrobacter* bacteria, was cultured in vitro to isolate vesicles, and then the vesicles were administered to inflammatory cells in vitro, it was confirmed that the secretion of inflammation mediators, mediated by pathogenic vesicles was significantly inhibited. Therefore, it is expected that the vesicles derived from *Enhydrobacter* bacteria according to the present invention can be effectively used for a method of diagnosing pancreatic cancer, cholangiocarcinoma, breast cancer, ovarian cancer, lymphoma, myocardial infarction, cardiomyopathy, atrial fibrillation, variant angina, liver cirrhosis, or diabetes, and a composition for preventing, alleviating or treating the diseases.

BEST MODES

Figure 1A:
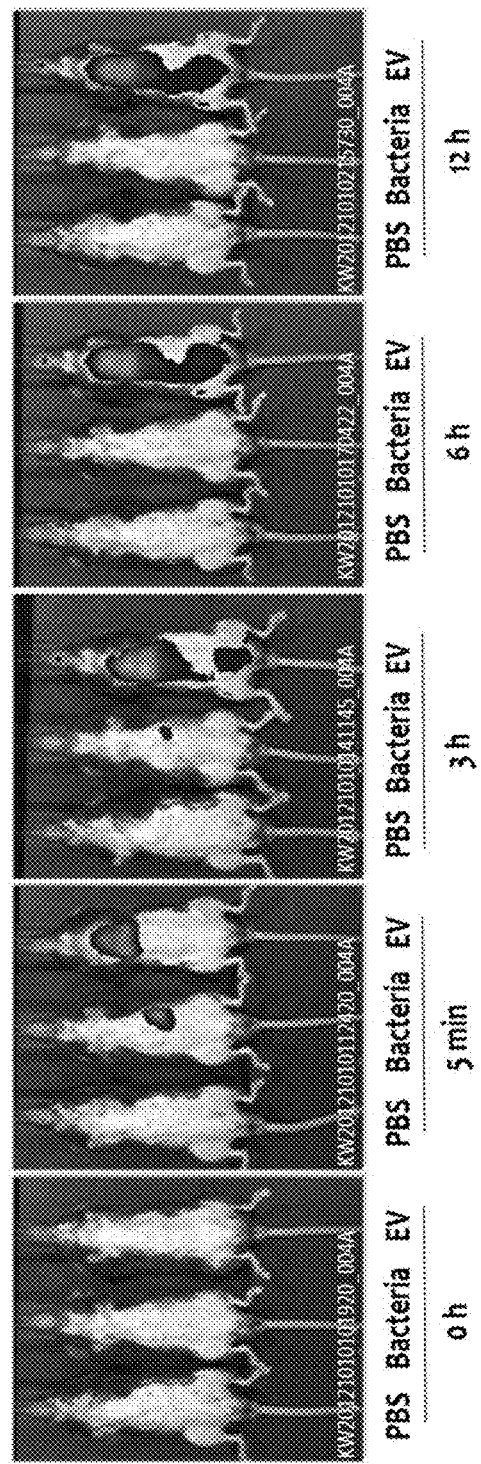
FIG. 1A is a series of photographs capturing distribution patterns of bacteria and bacteria-derived vesicles (EV) by time after the bacteria and the vesicles derived from bacteria were orally administered to mice.

The present invention relates to vesicles derived from *Enhydrobacter* bacteria and a use thereof.

The inventors confirmed that vesicles derived from *Enhydrobacter* bacteria are significantly reduced in clinical samples of patients with pancreatic cancer, cholangiocarcinoma, breast cancer, ovarian cancer, lymphoma, myocardial infarction, cardiomyopathy, atrial fibrillation, variant angina, liver cirrhosis, and diabetes, compared with a normal individual, through metagenomic analysis, thereby diagnosing a disease. In addition, as a result of isolating vesicles from *Enhydrobacter aerosaccus*, which is the only species belonging to *Enhydrobacter* bacteria and analyzing their characteristics, it was confirmed that these vesicles can be used in a composition for preventing, alleviating or treating a disease such as pancreatic cancer, cholangiocarcinoma, breast cancer, ovarian cancer, lymphoma, myocardial infarction, cardiomyopathy, atrial fibrillation, variant angina, chronic liver disease, and diabetes.

Thus, the present invention provides a method of providing information for diagnosing pancreatic cancer, cholangiocarcinoma, breast cancer, ovarian cancer, lymphoma, myocardial infarction, cardiomyopathy, atrial fibrillation, variant angina, liver cirrhosis, or diabetes, the method comprising the following steps:

(a) extracting DNAs from extracellular vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) classifying a case in which a content of extracellular vesicles derived from *Enhydrobacter* bacteria is lower than that of the normal individual sample, as pancreatic cancer, cholangiocarcinoma, breast cancer, ovarian cancer, lymphoma, myocardial infarction, cardiomyopathy, atrial fibrillation, variant angina, liver cirrhosis, or diabetes, through quantitative analysis of the PCR product.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether pancreatic cancer, cholangiocarcinoma, breast cancer, ovarian cancer, lymphoma, myocardial infarction, cardiomyopathy, atrial fibrillation, variant angina, liver cirrhosis, and/or diabetes occur, the level of the disease, and the like.

The term "nanovesicle" or "vesicle" as used herein refers to a structure consisting of a nano-sized membrane secreted from various bacteria. Vesicles derived from gram-negative bacteria or outer membrane vesicles (OMVs) have endotoxins (lipopolysaccharides), toxic protein, bacterial DNA and RNA, and vesicles derived from gram-positive bacteria also have peptidoglycan and lipoteichoic acid which are cell wall components of bacteria in addition to proteins and nucleic acids. In the present invention, nanovesicles or vesicles are secreted naturally from *Enhydrobacter* bacteria or produced artificially, are in the form of a sphere, and have an average diameter of 10 to 200 nm.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

In the present invention, the sample may be blood, but is not limited thereto.

Another aspect of the present invention provides a composition for preventing, treating or alleviating pancreatic cancer, cholangiocarcinoma, breast cancer, ovarian cancer, lymphoma, myocardial infarction, cardiomyopathy, atrial fibrillation, variant angina, chronic liver disease, or diabetes, comprising vesicles derived from *Enhydrobacter* bacteria as an active ingredient. The composition includes a food composition and a pharmaceutical composition, and in the present invention, the food composition includes a health functional food composition. The composition of the present invention may be a formulation of an oral spray or inhalant.

The term "prevention" as used herein refers to all actions that suppress pancreatic cancer, cholangiocarcinoma, breast cancer, ovarian cancer, lymphoma, myocardial infarction, cardiomyopathy, atrial fibrillation, variant angina, chronic liver disease, diabetes, and/or the like or delay the onset thereof via administration of the composition according to the present invention.

The term "treatment" as used herein refers to all actions that alleviate or beneficially change symptoms of pancreatic cancer, cholangiocarcinoma, breast cancer, ovarian cancer, lymphoma, myocardial infarction, cardiomyopathy, atrial fibrillation, variant angina, chronic liver disease, diabetes, and/or the like via administration of composition according to the present invention.

The term "alleviation" used as used herein refers to all actions that at least reduce a parameter associated with a condition to be treated, for example, the degree of symptoms.

The vesicles may be isolated from a culturing solution comprising *Enhydrobacter* bacteria by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be administered orally or parenterally (e.g., intravenously, subcutaneously, intradermally, intranasally or intratracheally) according to a desired method, and a dose may vary according to the condition and body weight of a patient, the severity of a disease, a drug formulation, an administration route, and duration, but may be suitably selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, an effective amount of the pharmaceutical composition according to the present invention may vary according to a patient's age, gender and body weight, and generally, the pharmaceutical composition may be administered at 0.001 to 150 mg, and preferably, 0.01 to 100 mg per kg of body weight daily or every two days, or 1 to 3 times daily. However, as the dose may be increased or decreased by an administration route, the severity of obesity, gender, a body weight or an age, the above-mentioned dose does not limit the scope of the present invention in any way.

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract, for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

In one embodiment of the present invention, as a result of orally administering bacteria and bacteria-derived vesicles to mice and observing in vivo absorption, distribution, and excretion patterns of the bacteria and the vesicles, it was confirmed that, while the bacteria were not absorbed via the intestinal mucous membrane, the bacteria-derived vesicles were absorbed within 5 minutes after administration and systemically distributed, and excreted via the kidneys, liver, and the like (see Example 1).

In another embodiment of the present invention, a bacterial metagenomic analysis was performed by using vesicles isolated from the blood of normal individuals who were matched in age and sex with patients with pancreatic cancer, cholangiocarcinoma, breast cancer, ovarian cancer, lymphoma, myocardial infarction, cardiomyopathy, atrial fibrillation, variant angina, liver cirrhosis, and diabetes. As a result, it was confirmed that vesicles derived from *Enhydrobacter* bacteria were significantly decreased in clinical samples of patients with pancreatic cancer, cholangiocarcinoma, breast cancer, ovarian cancer, lymphoma, myocardial infarction, cardiomyopathy, atrial fibrillation, variant angina, liver cirrhosis, and diabetes as compared to samples of normal individuals (see Examples 3 to 13).

In another embodiment of the present invention, *Enhydrobacter aerosaccus* was cultured to evaluate whether vesicles secreted therefrom have immunomodulatory and anti-inflammatory effects, and it was confirmed that IL-6 and TNF-α secretion caused by *Escherichia coli* vesicles (*E. coli* EVs) are effectively inhibited by *Enhydrobacter aerosaccus*-derived vesicles through evaluation of the secretion of inflammatory mediators by treating *E. coli* EVs, which are an inflammatory disease causative factor, following treatment of macrophages with various concentrations of *Enhydrobacter aerosaccus*-derived vesicles (refer to Example 14).

Hereinafter, preferred Examples for helping the understanding of the present invention will be suggested. However, the following Examples are provided only to more easily understand the present invention, and the contents of the present invention are not limited by the following Examples.

[Modes of the Invention]

EXAMPLES

Example 1. Analysis of In Vivo Absorption, Distribution, and Excretion Patterns of Intestinal Bacteria and Vesicles Derived from Bacteria In order to evaluate whether intestinal bacteria and bacteria-derived vesicles were systemically absorbed through the gastrointestinal tract, an experiment was performed with the following method. First, a dose of 50 μg of each of fluorescence-labeled intestinal bacteria and intestinal bacteria-derived vesicles was administered through the gastrointestinal tract to the stomach of a mouse, and fluorescence was measured after 0 minute, 5 minutes, 3 hours, 6 hours, and 12 hours. As a result of observing the entire image of the mouse, as illustrated in FIG. 1A, the bacteria were not systemically absorbed, but the vesicles derived from bacteria were systemically absorbed 5 minutes after administration, and fluorescence was strongly observed in the bladder 3 hours after administration, so that it could be seen that the vesicles were excreted to the urinary tract. Further, it could be seen that the vesicles were present in the body until 12 hours after administration.

Figure 1B:
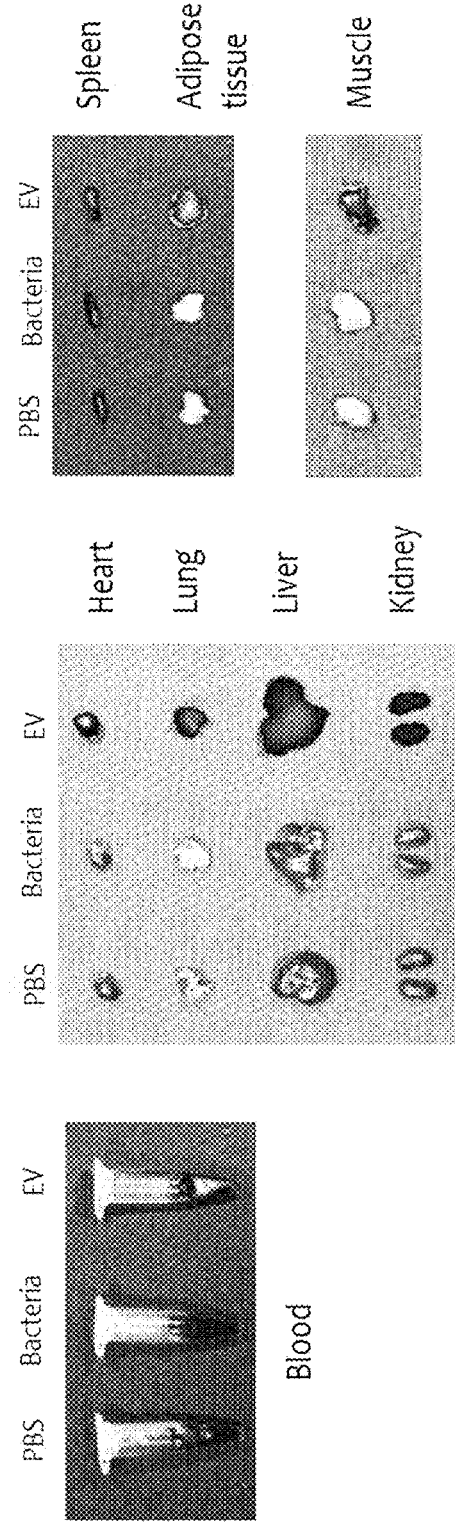
FIG. 1B is a result of evaluating the in vivo distribution patterns of the bacteria and the vesicles by harvesting blood, kidneys, liver, and various organs at 12 hours after orally administering the bacteria and the vesicles.

In addition, in order to evaluate the pattern in which the intestinal bacteria and the vesicles derived from the intestinal bacteria infiltrated into various organs after they were systemically absorbed, 50 μg of bacteria and vesicles derived from bacteria labeled with fluorescence were administered in the same manner as described above, and then the blood, heart, lungs, liver, kidneys, spleen, fat, and muscle were collected 12 hours after administration. As a result of observing fluorescence in the collected tissues, as illustrated in FIG. 1B, it could be seen that the vesicles derived from bacteria were distributed in the blood, heart, lungs, liver, spleen, fat, muscle, and kidneys but the bacteria were not absorbed.

Example 2. Metagenomic Analysis of Vesicles Derived from Bacteria in Clinical Sample After blood sample was first put into a 10-ml tube and suspended matter was allowed to settle by a centrifuge (3,500×g, 10 min, 4° C.), only the supernatant was transferred to a new 10-ml tube. After bacteria and impurities were removed by using a 0.22-μm filter, they were transferred to a Centriprep tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-μm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 μl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

TABLE 1

| primer | | Sequence | SEQ ID No. |
|---|---|---|---|
| 16S rDNA | 16S_V3_F | 5'-TCGTCGGCAGCGTCAGATGTGTATAAGA GACAGCCTACGGGNGGCWGCAG-3' | 1 |
| | 16S_V4_R | 5'-GTCTCGTGGGCTCGGAGATGTGTATAAG AGACAGGACTACHVGGGTATCTAATCC | 2 |

The DNA extracted by the above method was amplified using the 16S rDNA primers, and then sequencing was performed (Illumina MiSeq sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the OTU (operational taxonomy unit) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Figure 2:
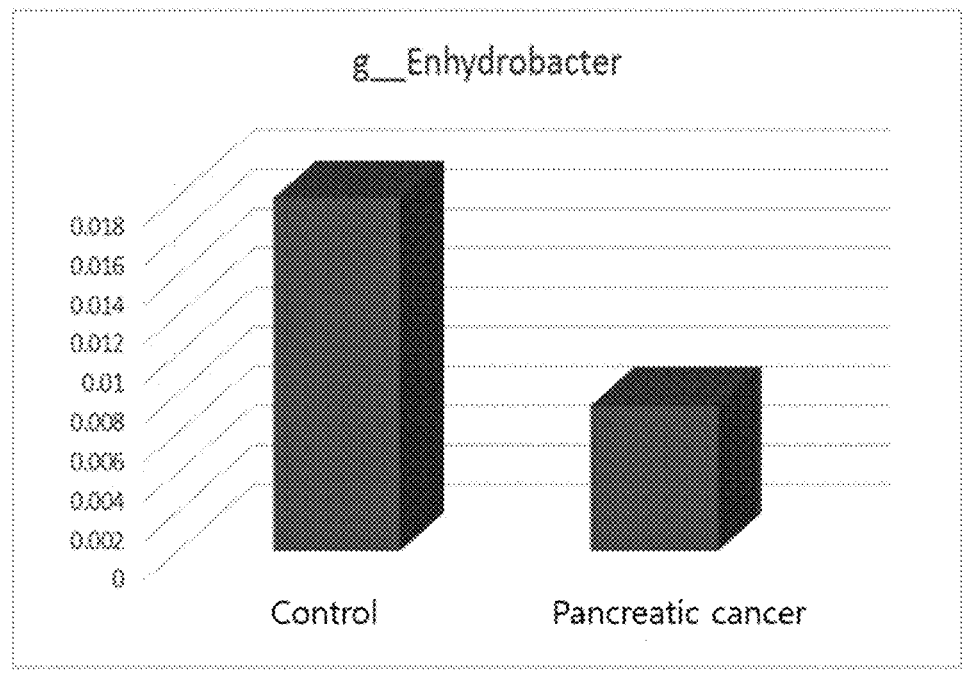
FIG. 2 is a result of comparing the distributions of vesicles derived from *Enhydrobacter* bacteria after metagenomic analysis of bacteria-derived vesicles present in the blood of pancreatic cancer patients and a normal individual.

Example 3. Metagenomic Analysis of Bacteria-Derived Vesicles in Blood of Patient with Pancreatic Cancer After a metagenomic analysis was performed using the method of Example 2 on the blood from 176 patients with pancreatic cancer, and 271 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with pancreatic cancer as compared to the blood from the normal individuals (see Table 2 and FIG. 2).

TABLE 2

| Blood | Control | | Pancreatic cancer | | t-test | |
|---|---|---|---|---|---|---|
| Taxon | Mean | SD | Mean | SD | p-value | Ratio |
| g_Enhydrobacter | 0.0179 | 0.0228 | 0.0074 | 0.0075 | <0.0001 | 0.41 |

Figure 3:
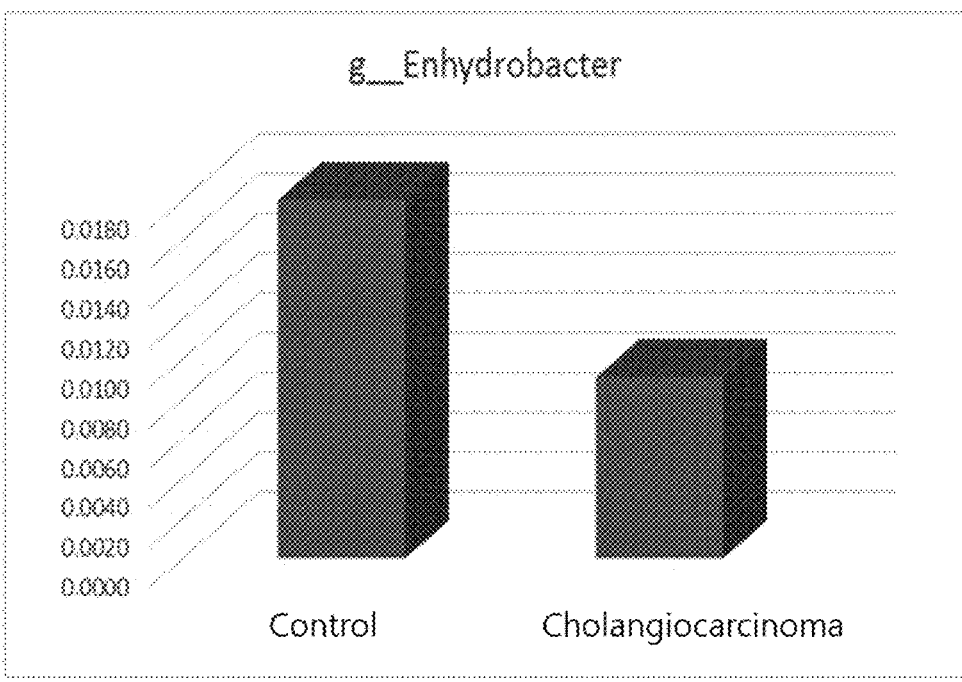
FIG. 3 is a result of comparing the distributions of vesicles derived from *Enhydrobacter* bacteria after metagenomic analysis of bacteria-derived vesicles present in the blood of cholangiocarcinoma patients and a normal individual.

Example 4. Metagenomic Analysis of Bacteria-Derived Vesicles in Blood of Patient with Cholangiocarcinoma After a metagenomic analysis was performed using the method of Example 2 on the blood from 79 patients with cholangiocarcinoma, and 259 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with cholangiocarcinoma as compared to the blood from the normal individuals (see Table 3 and FIG. 3).

TABLE 3

| Blood | Control | | Cholangio-carcinoma | | t-test | |
|---|---|---|---|---|---|---|
| Taxon | Mean | SD | Mean | SD | p-value | Ratio |
| g_Enhydrobacter | 0.0180 | 0.0229 | 0.0091 | 0.0158 | 0.0002 | 0.51 |

Figure 4:
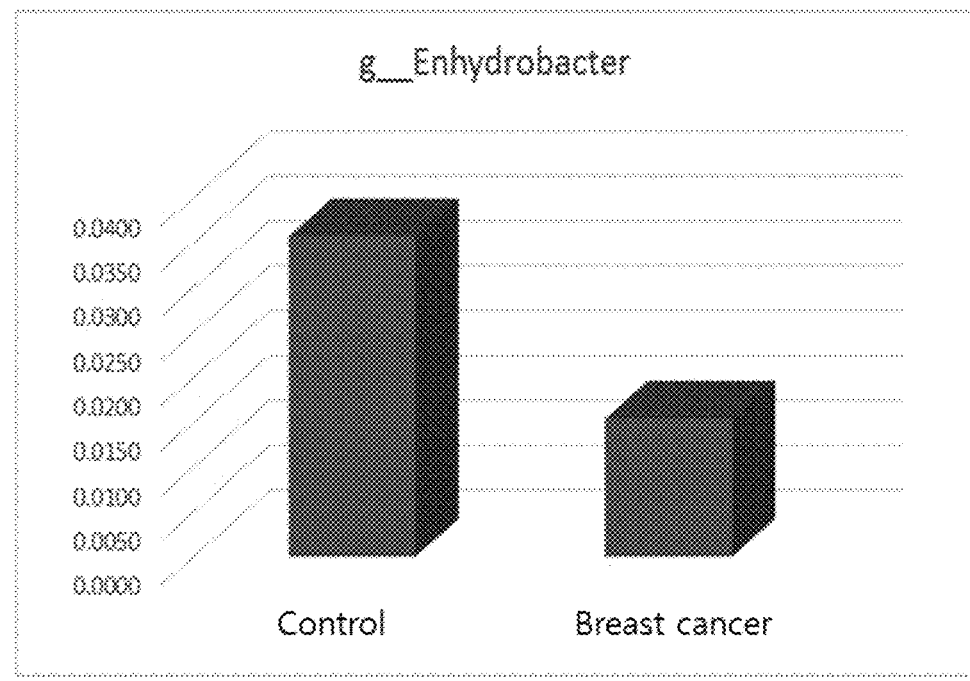
FIG. 4 is a result of comparing the distributions of vesicles derived from *Enhydrobacter* bacteria after metagenomic analysis of bacteria-derived vesicles present in the blood of breast cancer patients and a normal individual.

Example 5. Metagenomic Analysis of Bacteria-Derived Vesicles in Blood of Patient with Breast Cancer After a metagenomic analysis was performed using the method of Example 2 on the blood from 96 patients with breast cancer, and 192 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with breast cancer as compared to the blood from the normal individuals (see Table 4 and FIG. 4).

TABLE 4

| Blood | Control | | Breast cancer | | t-test | |
|---|---|---|---|---|---|---|
| Taxon | Mean | SD | Mean | SD | p-value | Ratio |
| g_Enhydrobacter | 0.0357 | 0.0445 | 0.0154 | 0.0122 | <0.0001 | 0.43 |

Figure 5:
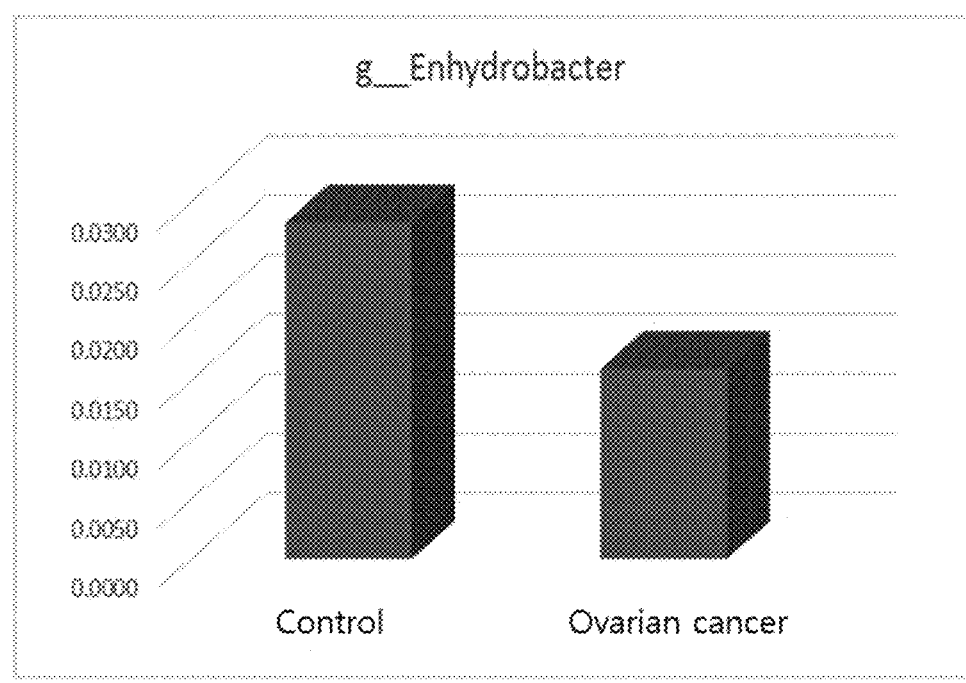
FIG. 5 is a result of comparing the distributions of vesicles derived from *Enhydrobacter* bacteria after metagenomic analysis of bacteria-derived vesicles present in the blood of ovarian cancer patients and a normal individual.

Example 6. Metagenomic Analysis of Bacteria-Derived Vesicles in Blood of Patient with Ovarian Cancer After a metagenomic analysis was performed using the method of Example 2 on the blood from 137 patients with ovarian cancer, and 139 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with ovarian cancer as compared to the blood from the normal individuals (see Table 5 and FIG. 5).

TABLE 5

| Blood | Control | | Ovarian cancer | | t-test | |
|---|---|---|---|---|---|---|
| Taxon | Mean | SD | Mean | SD | p-value | Ratio |
| g_Enhydrobacter | 0.0283 | 0.0500 | 0.0160 | 0.0237 | 0.0097 | 0.57 |

Figure 6:
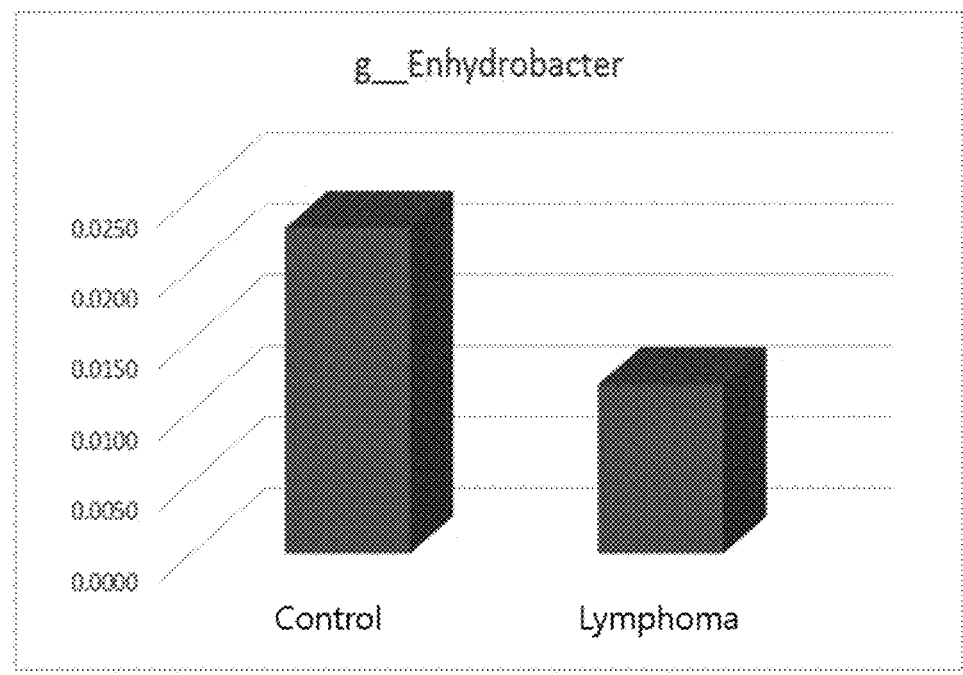
FIG. 6 is a result of comparing the distributions of vesicles derived from *Enhydrobacter* bacteria after metagenomic analysis of bacteria-derived vesicles present in the blood of lymphoma patients and a normal individual.

Example 7. Metagenomic Analysis of Bacteria-Derived Vesicles in Blood of Patient with Lymphoma After a metagenomic analysis was performed using the method of Example 2 on the blood from 63 patients with lymphoma, and 53 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with lymphoma as compared to the blood from the normal individuals (see Table 6 and FIG. 6).

TABLE 6

| Blood | Control | | Lymphoma | | t-test | |
|---|---|---|---|---|---|---|
| Taxon | Mean | SD | Mean | SD | p-value | Ratio |
| g_Enhydrobacter | 0.0229 | 0.0228 | 0.0119 | 0.0112 | 0.0023 | 0.52 |

Figure 7:
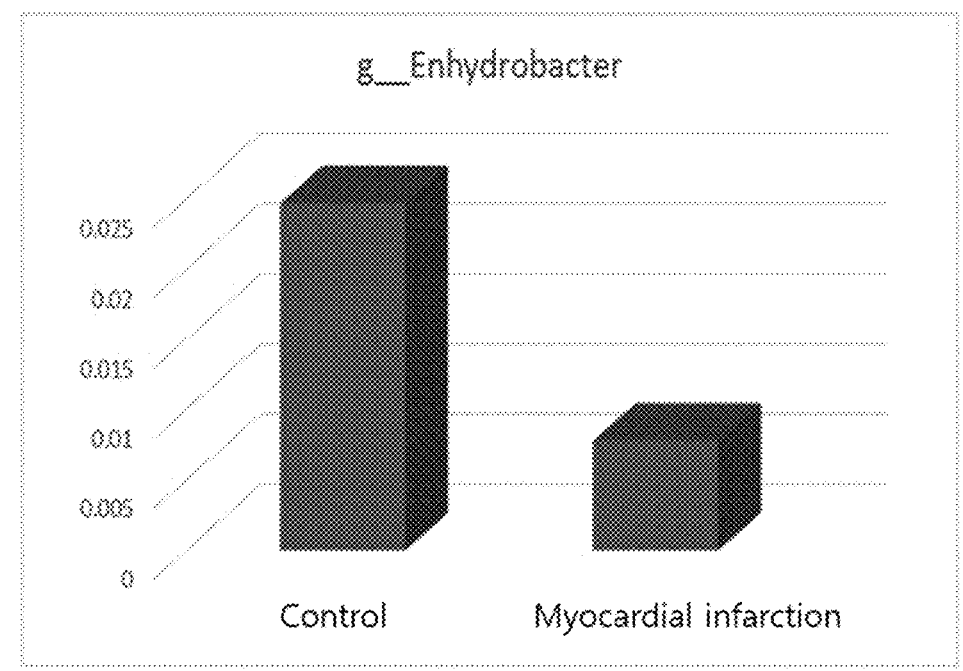
FIG. 7 is a result of comparing the distributions of vesicles derived from *Enhydrobacter* bacteria after metagenomic analysis of bacteria-derived vesicles present in the blood of myocardial infarction patients and a normal individual.

Example 8. Metagenomic Analysis of Bacteria-Derived Vesicles in Blood of Patient with Myocardial Infarction After a metagenomic analysis was performed using the method of Example 2 on the blood from 57 patients with myocardial infarction, and 163 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with myocardial infarction as compared to the blood from the normal individuals (see Table 7 and FIG. 7).

TABLE 7

| Blood | Control | | Myocardial infarction | | t-test | |
|---|---|---|---|---|---|---|
| Taxon | Mean | SD | Mean | SD | p-value | Ratio |
| g_Enhydrobacter | 0.0247 | 0.0524 | 0.0078 | 0.0234 | 0.0012 | 0.31 |

Figure 8:
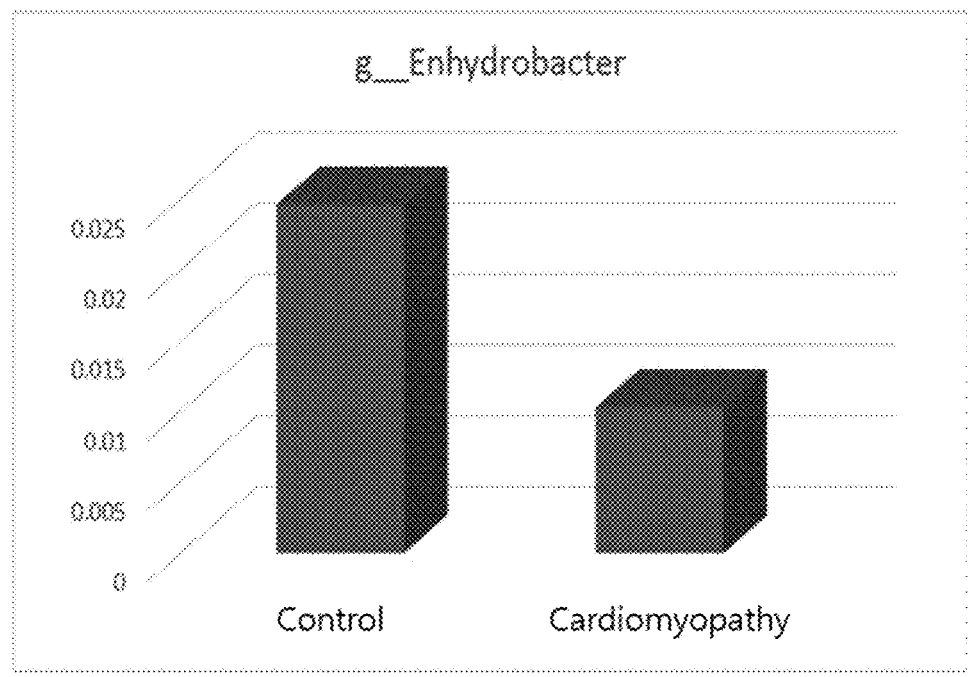
FIG. 8 is a result of comparing the distributions of vesicles derived from *Enhydrobacter* bacteria after metagenomic analysis of bacteria-derived vesicles present in the blood of cardiomyopathy patients and a normal individual.

Example 9. Metagenomic Analysis of Bacteria-Derived Vesicles in Blood of Patient with Cardiomyopathy After a metagenomic analysis was performed using the method of Example 2 on the blood from 72 patients with cardiomyopathy, and 163 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with cardiomyopathy as compared to the blood from the normal individuals (see Table 8 and FIG. 8).

TABLE 8

| Blood | Control | | Cardio-myopathy | | t-test | |
|---|---|---|---|---|---|---|
| Taxon | Mean | SD | Mean | SD | p-value | Ratio |
| g_Enhydrobacter | 0.0246 | 0.0524 | 0.0103 | 0.0142 | 0.0015 | 0.42 |

Figure 9:
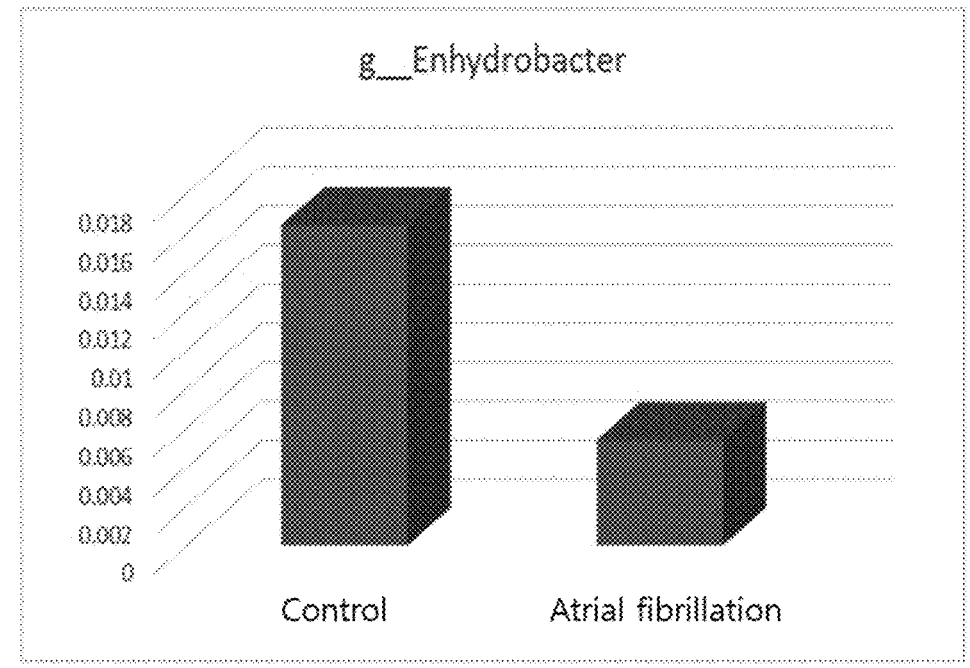
FIG. 9 is a result of comparing the distributions of vesicles derived from *Enhydrobacter* bacteria after metagenomic analysis of bacteria-derived vesicles present in the blood of atrial fibrillation patients and a normal individual.

Example 10. Metagenomic Analysis of Bacteria-Derived Vesicles in Blood of Patient with Atrial Fibrillation After a metagenomic analysis was performed using the method of Example 2 on the blood from 34 patients with atrial fibrillation, and 62 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with atrial fibrillation as compared to the blood from the normal individuals (see Table 9 and FIG. 9).

TABLE 9

| Blood | Control | | Atrial fibrillation | | t-test | |
|---|---|---|---|---|---|---|
| Taxon | Mean | SD | Mean | SD | p-value | Ratio |
| g_Enhydrobacter | 0.0164 | 0.0217 | 0.0054 | 0.0058 | 0.0003 | 0.33 |

Figure 10:
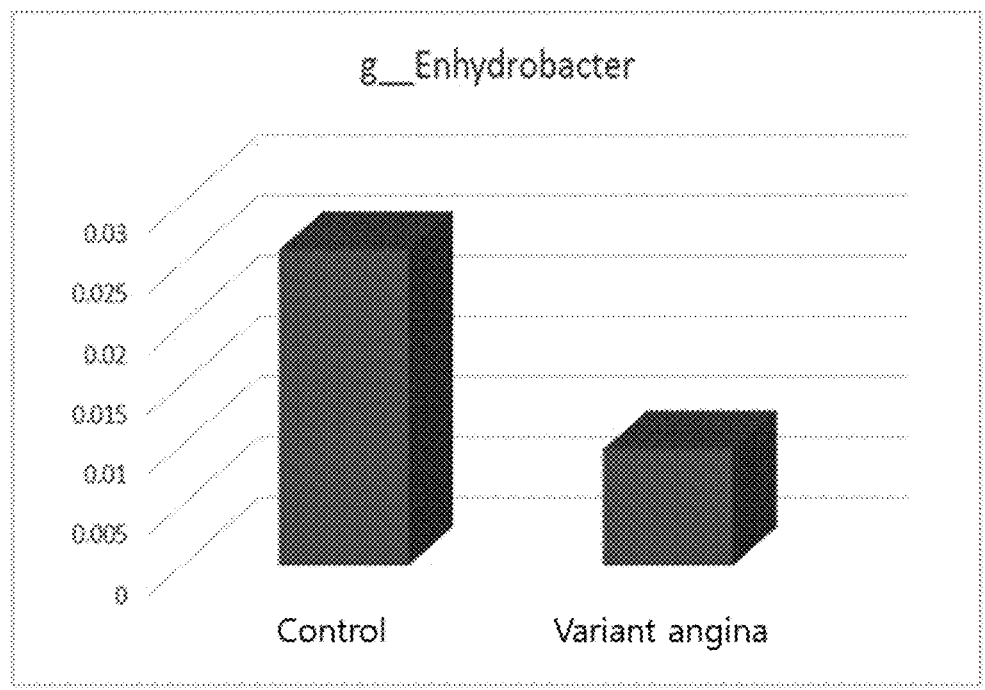
FIG. 10 is a result of comparing the distributions of vesicles derived from *Enhydrobacter* bacteria after metagenomic analysis of bacteria-derived vesicles present in the blood of variant angina patients and a normal individual.

Example 11. Metagenomic Analysis of Bacteria-Derived Vesicles in Blood of Patient with Variant Angina After a metagenomic analysis was performed using the method of Example 2 on the blood from 80 patients with variant angina, and 80 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with variant angina as compared to the blood from the normal individuals (see Table 10 and FIG. 10).

TABLE 10

| Blood | Control | | Variant angina | | t-test | |
|---|---|---|---|---|---|---|
| Taxon | Mean | SD | Mean | SD | p-value | Ratio |
| g_Enhydrobacter | 0.0261 | 0.0579 | 0.0096 | 0.0164 | 0.0167 | 0.37 |

Figure 11:
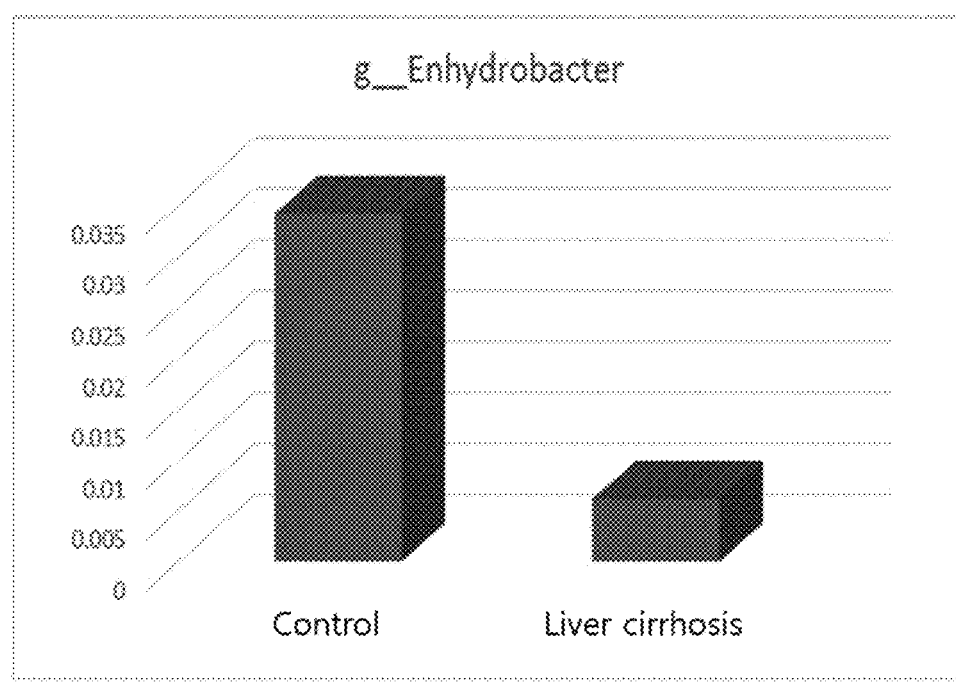
FIG. 11 is a result of comparing the distributions of vesicles derived from *Enhydrobacter* bacteria after metagenomic analysis of bacteria-derived vesicles present in the blood of liver cirrhosis patients and a normal individual.

Example 12. Metagenomic Analysis of Bacteria-Derived Vesicles in Blood of Patient with Liver Cirrhosis After a metagenomic analysis was performed using the method of Example 2 on the blood from 130 patients with liver cirrhosis, and 145 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with liver cirrhosis as compared to the blood from the normal individuals (see Table 11 and FIG. 11).

TABLE 11

| Blood | Control | | Liver cirrhosis | | t-test | |
|---|---|---|---|---|---|---|
| Taxon | Mean | SD | Mean | SD | p-value | Ratio |
| g_Enhydrobacter | 0.0342 | 0.0781 | 0.0061 | 0.0164 | 0.0005 | 0.18 |

Figure 12:
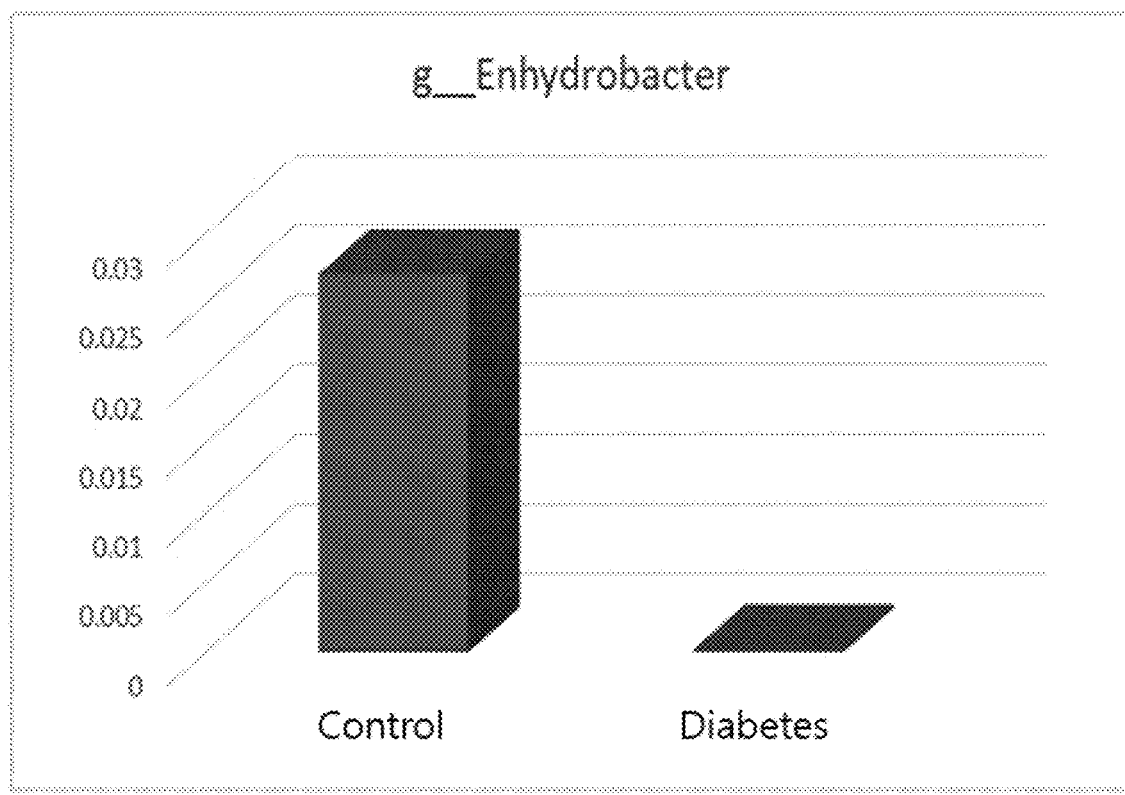
FIG. 12 is a result of comparing the distributions of vesicles derived from *Enhydrobacter* bacteria after metagenomic analysis of bacteria-derived vesicles present in the blood of diabetes patients and a normal individual.

Example 13. Metagenomic Analysis of Bacteria-Derived Vesicles in Blood of Patient with Diabetes After a metagenomic analysis was performed using the method of Example 2 on the blood from 61 patients with diabetes, and 122 normal individuals who were matched in age and sex by extracting genes from vesicles present in the blood, the distribution of vesicles derived from *Enhydrobacter* bacteria was evaluated. As a result, it was confirmed that vesicles derived from *Enhydrobacter* bacteria were significantly decreased in the blood from the patients with diabetes as compared to the blood from the normal individuals (see Table 12 and FIG. 12).

TABLE 12

| Blood | Control | | Diabetes | | t-test | |
|---|---|---|---|---|---|---|
| Taxon | Mean | SD | Mean | SD | p-value | Ratio |
| g_Enhydrobacter | 0.0271 | 0.0286 | 0.0002 | 0.0002 | <0.0001 | 0.01 |

Example 14. Anti-Inflammatory Effects of
*Enhydrobacter Aerosaccus*-Derived Vesicles Based on the results of the above examples, an *Enhydrobacter aerosaccus* strain belonging to *Enhydrobacter* bacteria was isolated from an environmental sample and cultured, followed by isolation of vesicles thereof. The *Enhydrobacter aerosaccus* strain was incubated in a brain heart infusion (BHI) medium until an absorbance ($OD_{600}$) reached 1.0 to 1.5 at 37° C. in an aerobic chamber, and then sub-cultured. Afterward, a medium supernatant which does not contain the strain was collected, centrifuged at 10,000 g and 4° C. for 15 minutes, and filtered through a 0.45-μm filter. A supernatant obtained thereby was concentrated to a volume of 200 mL through ultrafiltration using a QuixStand benchtop system (GE Healthcare, UK) as a 100 kDa hollow filter membrane. Subsequently, the concentrated supernatant was filtered once again with a 0.22-μm filter and ultracentrifuged at 150,000 g and 4° C. for 3 hours, followed by suspension of a pellet in DPBS. Afterward, density gradient centrifugation was performed using 10%, 40% and 50% OptiPrep solutions (Axis-Shield PoC AS, Norway), and to prepare low-density solutions, the OptiPrep solutions were diluted with HEPES-buffered saline (20 mM HEPES, 150 mM NaCl, pH 7.4) before use. After centrifugation for 2 hours under conditions of 200,000 g and 4° C., each solution fractionated with an equal volume of 1 mL from the top layer was additionally ultracentrifuged for 3 hours under conditions of 150,000 g and 4° C. Afterward, a protein was quantified using a bicinchoninic acid (BCA) assay, and an experiment was performed on vesicles obtained as described above.

To examine the effect of the *Enhydrobacter aerosaccus*-derived vesicles on the secretion of inflammatory mediators from inflammatory cells, a mouse macrophage cell line, Raw 264.7 cells, was treated with *Enhydrobacter aerosaccus*-derived vesicles at various concentrations (0.1, 1, 10 μg/mL), and secretion amounts of inflammatory mediators (IL-6 and TNF-α) were measured by treating vesicles derived from *Escherichia coli* (*E. coli* EV) which are vesicles for inflammatory disease pathogenesis. In addition, as a useful control vesicle, *Lactobasillus plantarum*-derived vesicles (1 μg/mL) were used. More specifically, the Raw 264.7 cells were seeded in a 24-well cell culture plate at $1 \times 10^5$ per well, and incubated in DMEM for 24 hours. Afterward, a culture supernatant was collected in a 1.5 mL tube, centrifuged at 3000 g for 5 minutes, thereby collecting a supernatant. The supernatant was stored at 4° C., followed by ELISA.

Figure 13:
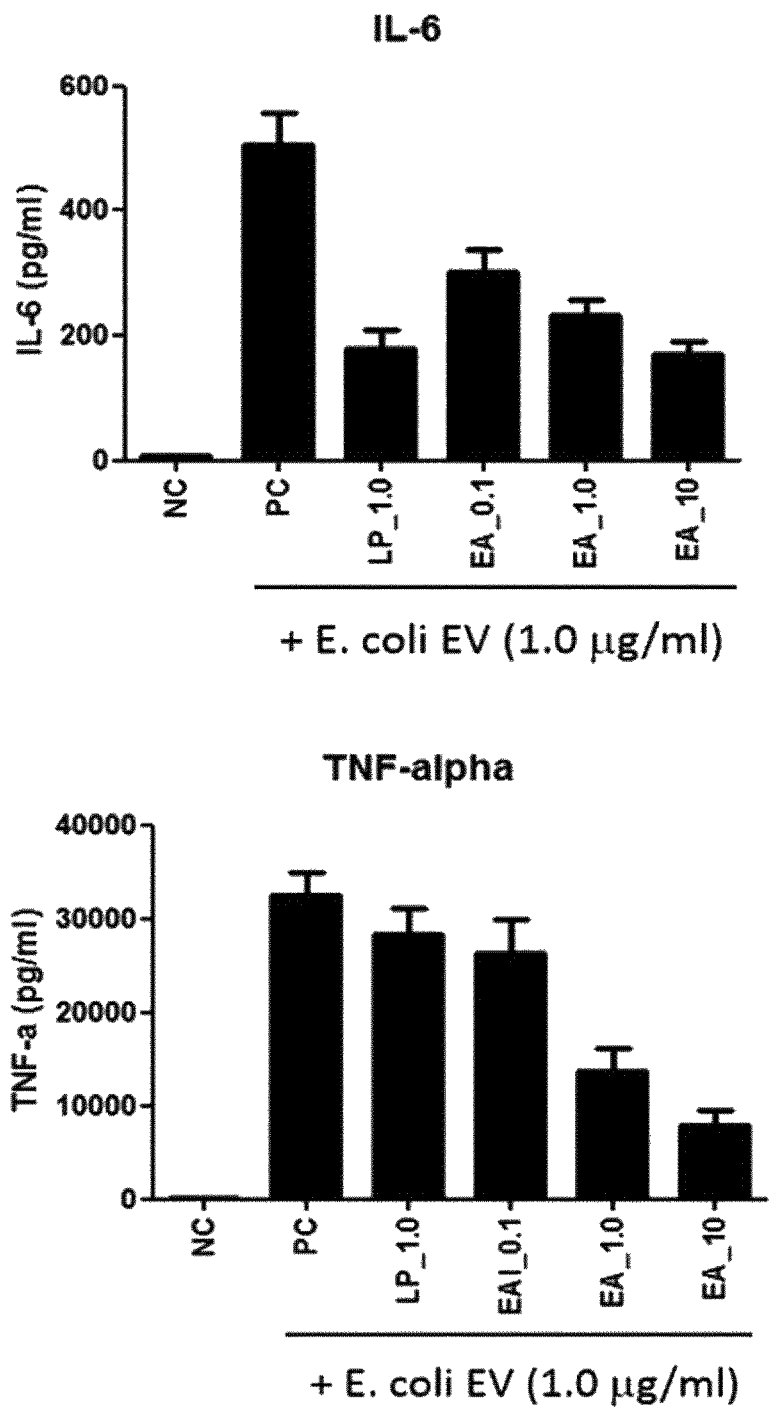
FIG. 13 is a result of evaluating an effect on the secretion of IL-6 and TNF-α which inflammatory mediators caused by *E. coli* EVs by pretreating vesicles derived from *Enhydrobacter* bacteria before treatment of pathogenic vesicles such as *E. coli* EVs to evaluate anti-inflammatory and immunomodulatory effects of *Enhydrobacter aerosaccus*-derived vesicles (PC: positive control; LP: *Lactobacillus plantarum* EVs; EA: *Enhydrobacter aerosaccus* EVs).

As a result, when *Enhydrobacter aerosaccus*-derived vesicles were pretreated, it was confirmed that the secretion of the IL-6 and TNF-α by *E. coli* EVs was significantly suppressed (see FIG. 13). Particularly, *Enhydrobacter aerosaccus* vesicles significantly inhibited TNF-α secretion, compared with *Lactobasillus plantarum* vesicles. This means that *Enhydrobacter aerosaccus*-derived vesicles can effectively inhibit immune dysfunction and inflammation induced by pathogenic vesicles such as *E. coli*-derived vesicles.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

Since vesicles derived from *Enhydrobacter* bacteria according to the present invention may be used in a method of diagnosing pancreatic cancer, cholangiocarcinoma, breast cancer, ovarian cancer, lymphoma, myocardial infarction, cardiomyopathy, atrial fibrillation, variant angina, liver cirrhosis, or diabetes, and a composition for preventing, alleviating or treating the disease, they are expected to be effectively used in related medical and food industry fields.

The invention claimed is:

1. A method of suppressing inflammation, the method comprising administering to a subject in need thereof a pharmaceutical composition comprising an effective amount of vesicles derived from *Enhydrobacter* bacteria.

2. The method of claim 1, wherein the vesicles have an average diameter of 10 to 200 nm.

3. The method of claim 1, wherein the vesicles are secreted naturally or artificially from *Enhydrobacter* bacteria.

4. The method of claim 1, wherein the vesicles derived from *Enhydrobacter* bacteria are vesicles derived from *Enhydrobacter aerosaccus*.

* * * * *

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)
<223> OTHER INFORMATION: a or g or c or t/u

<400> SEQUENCE: 1
tcgtcggcag cgtcagatgt gtataagaga cagcctacgg gnggcwgcag            50

```
<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc    55
```